United States Patent
Tsukuno et al.

(10) Patent No.: US 6,632,956 B2
(45) Date of Patent: Oct. 14, 2003

(54) PREPARATION OF DIORGANODICHLOROSILANE

(75) Inventors: Akihito Tsukuno, Annaka (JP); Hiroyuki Kobayashi, Annaka (JP); Yukinori Satoh, Annaka (JP); Hideaki Ozeki, Annaka (JP); Yoshihiro Shirota, Tokyo (JP); Susumu Ueno, Takefu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/218,558

(22) Filed: Aug. 15, 2002

(65) Prior Publication Data

US 2003/0109735 A1 Jun. 12, 2003

(30) Foreign Application Priority Data

Aug. 17, 2001 (JP) .......................................... 2001-247800

(51) Int. Cl.$^7$ .................................................. C07F 7/04
(52) U.S. Cl. ....................................................... 556/469
(58) Field of Search ........................................... 556/469

(56) References Cited

U.S. PATENT DOCUMENTS

| 2,647,136 A | 7/1953 | Sauer |
| 2,647,912 A | 8/1953 | Barry et al. |
| 4,447,631 A | 5/1984 | Faure et al. |
| 4,552,973 A | 11/1985 | Feldner et al. |

*Primary Examiner*—Samuel Barts
(74) *Attorney, Agent, or Firm*—Birch, Stewart, Kolasch & Birch, LLP

(57) ABSTRACT

A diorganodichlorosilane is prepared by subjecting organochlorosilanes to disproportionation reaction in the co-presence of a SiH group-containing compound and in the presence of a primary catalyst of $AlCl_3$ or $AlBr_3$ and a co-catalyst of Mg, Al, Ca, Ti, Fe, Ni, Cu, Zn or Sn or a compound thereof. The invention enables disproportionation reaction of organochlorosilanes under atmospheric pressure and at a low temperature at which no substantial sublimation of $AlCl_3$ or the like occurs, thus allowing the reaction equipment to be simple and improving the safety of reaction.

11 Claims, No Drawings

PREPARATION OF DIORGANODICHLOROSILANE

This invention relates to a process for preparing a diorganodichlorosilane through disproportionation reaction of organochlorosilanes.

BACKGROUND OF THE INVENTION

In the industry, organochlorosilanes are generally produced by direct synthesis known as Rochow method. This reaction yields diorganodichlorosilane of the most interest as a main product and by-products such as organotrichloro silane, triorganochlorosilane, and organodichlorosilane which are less useful and superfluous. There are additionally formed low-boiling fractions and high-boiling fractions such as disilanes, which must be discarded in a substantial sense.

As a solution to this problem, U.S. Pat. Nos. 2,647,136, 2,647,912, 4,447,631 and 4,552,973 propose to convert less useful organochlorosilanes to more useful organochloro silanes in the presence of a Lewis acid or a Lewis acid and a SiH group-containing compound. The most difficulty with these methods resides in the sublimation of $AlC_3$ used as the Lewis acid. Due to a low reaction rate, reaction must be effected at high temperature and high pressure for a long time, raising a safety problem.

SUMMARY OF THE INVENTION

Therefore, an object of the present invention is to provide a process for preparing a useful diorganodichloro silane in a high yield from less useful organochlorosilanes through reaction at a low temperature and a high rate.

It has been found that when an organochlorosilane is subjected to disproportionation reaction in the co-presence of a compound having a hydrogen atom directly bonded to a silicon atom and in the presence of a primary catalyst of $AlCl_3$ or $AlBr_3$ and a co-catalyst of a specific metal or metal compound, this reaction takes place at a high rate even at atmospheric pressure and a low temperature (at which sublimation of $AlCl_3$ or $AlBr_3$ gives rise to no substantial problem), thereby yielding a useful diorganodichlorosilane.

The present invention provides a process for preparing a diorganodichlorosilane, comprising the step of subjecting an organochlorosilane to disproportionation reaction in the co-presence of a compound having a hydrogen atom directly bonded to a silicon atom and in the presence of a primary catalyst of $AlC_3$ or $AlBr_3$ and a co-catalyst selected from the group consisting of Mg, Al, Ca, Ti, Fe, Ni, Cu, Zn and Sn, compounds of these metals excluding $AlCl_3$ and $AlBr_3$, and mixtures thereof.

DESCRIPTION OF THE PREFERRED EMBODIMENT

The process of the present invention starts with organochlorosilanes which are silane compounds having an organic group and/or a chlorine atom bonded to a silicon atom, for example, monoorganotrichlorosilanes, triorgano monochlorosilanes, tetrachlorosilane, tetraorganosilanes, and disilanes.

The organochlorosilanes may be used alone or in admixture of two or more. Inclusion of a diorganodichloro silane in the organochlorosilane mixture is acceptable. It is preferred to use an organotrichlorosilane such as methyltrichlorosilane and a triorganochlorosilane such as trimethylchlorosilane as the starting charge. The proportion of these organochlorosilanes in the starting charge is not critical because the invention is also directly applicable to crude silanes. When organochloro silanes in the starting charge are selected and adjusted, a proper choice is made on a stoichiometric basis so as to produce a maximum amount of diorganodichlorosilane.

The organic groups on the organochlorosilanes are preferably monovalent hydrocarbon groups having 1 to 6 carbon atoms, for example, alkyl groups such as methyl and ethyl and aryl groups such as phenyl. Of these, methyl, ethyl and phenyl are preferred, with methyl being most preferred.

The compound having a hydrogen atom directly bonded to a silicon atom, which is referred to as SiH group-containing compound, hereinafter, is not critical as long as it has a SiH group. Preferably it is an organosilane compound having the following general formula:

$$R_aH_bSiCl_{4-a-b}$$

wherein R is a monovalent hydrocarbon group preferably of 1 to 6 carbon atoms, more preferably methyl, ethyl or phenyl, most preferably methyl, "a" is an integer of 0 to 3, "b" is an integer of 1 to 4, and a+b is an integer of 1 to 4. Illustrative are methyldichlorosilane and dimethylchloro silane, with methyldichlorosilane being most preferred.

The SiH group-containing compounds may be used alone or in admixture of two or more. An appropriate amount of the SiH group-containing compound used is 0.01 to 50 parts, more preferably 0.1 to 30 parts, most preferably 1 to 25 parts by weight per 100 parts by weight of the organochloro silane charge.

It is noted that the organochlorosilane and the SiH group-containing compound may be individually added to the reaction system, although a mixture of organochlorosilanes etc. Resulting from the manufacture of organochlorosilane (typically by Rochow method) may be used.

In the present invention, $AlCl_3$ or $AlBr_3$ is used as the primary catalyst, with $AlC_3$ being most preferred. An appropriate amount of the primary catalyst used is 0.01 to 50 parts, more preferably 0.1 to 30 parts, most preferably 1 to 25 parts by weight per 100 parts by weight of the organochlorosilane charge.

In addition to the primary catalyst, the present invention uses a co-catalyst selected from among the metals Mg, Al, Ca, Ti, Fe, Ni, Cu, Zn and Sn, compounds of these metals excluding $AlCl_3$ and $AlBr_3$, and mixtures thereof. The metal compounds include alloys, oxides, hydroxides, chlorides, carbonates, and sulfates. Exemplary of the metal compounds are magnesium oxide, aluminum oxide, calcium oxide, titanium oxide, iron oxide, nickel oxide, copper oxide, zinc oxide, tin oxide, calcium hydroxide, magnesium chloride, zinc chloride, magnesium carbonate, magnesium sulfate, and brass. Of these, magnesium, magnesium oxide, magnesium chloride, zinc oxide, calcium oxide, calcium hydroxide, zinc chloride and brass are preferred, with magnesium oxide being most preferred.

An appropriate amount of the co-catalyst used is 0.1 to 20 parts, more preferably 1 to 10 parts by weight per 100 parts by weight of the organochlorosilane charge and 1 to 50 parts, more preferably 2 to 30 parts by weight per 100 parts by weight of the primary catalyst. Outside the range, a smaller amount of the co-catalyst may fail to achieve the desired effect whereas a larger amount of the co-catalyst may give a reaction system which contains too much solid components and is difficult to handle.

In the practice of the invention, disproportionation reaction may be carried out on the organochlorosilane charge in the presence of the aforementioned components. In a preferred embodiment using a mixture of methyltrichloro silane and trimethylchlorosilane as the organochlorosilane, dimethyldichlorosilane which is most useful in the silicone manufacture can be produced in high yields.

The reaction may be carried out in any desired way, typically in a well-known way, for example, by mixing the aforementioned components in a reactor and conducting reaction while stirring. The reaction temperature is preferably a temperature at which no substantial sublimation of $AlCl_3$ or the like occurs, for example, 100° C. or lower, and especially 80° C. or lower. The lower limit of reaction temperature is not critical and preferably at or above room temperature (e.g., 25° C.). With respect to the pressure, the reaction takes place even under atmospheric pressure although some pressure may be applied for accelerating the reaction.

EXAMPLE

Examples of the invention are given below by way of illustration and not by way of limitation.

Examples 1–23 and Comparative Examples 1–3

A reactor equipped with a stirrer and a reflux condenser having a dry ice trap was charged with 150 g of trimethylchlorosilane (KA31) and 150 g of methyltrichloro silane (KA13) as the organochlorosilane, methyldichloro silane (KA12) as the SiH group-containing compound, $AlCl_3$ ($AlBr_3$ in Example 17) as the primary catalyst, and a co-catalyst, the amounts of the latter three being shown in Tables 1 to 4. With stirring, reaction was effected under full reflux conditions.

Heating was completed within one hour and the reaction time was 5 hours (13 hours in Comparative Example 2). It is noted that in Example 1 and Comparative Example 2, a sample was taken from the reaction solution midway the reaction at the indicated time in Tables 1 and 4 and analyzed for composition by a method to be described later. The reaction temperature rose to a range of 50–80° C. as the amount of dimethyldichlorosilane (KA22) increased. After the completion of reaction, the reaction system was cooled to room temperature within one hour.

Compositional analysis of the charge and the reaction solution was carried out by gas chromatography. From these results, the yield of dimethyldichlorosilane (KA22) was computed. The composition of the reaction solution is shown in Tables 1 to 4 together with the yield.

TABLE 1

| | Example | | | | | | | |
|---|---|---|---|---|---|---|---|---|
| | 1 | 2 | 3 | 4 | 5 | 6 | 7 | 8 |
| Co-catalyst | MgO | MgO | MgO | MgO | MgO | $MgCl_2$ | CaO powder | $ZnCl_2$ |
| Reaction time (hr) | 1 | 5 | 5 | 5 | 5 | 5 | 5 | 5 |
| Charge (g) | | | | | | | | |
| KA31 | 150 | 150 | 150 | 150 | 150 | 150 | 150 | 150 |
| KA13 | 150 | 150 | 150 | 150 | 150 | 150 | 150 | 150 |
| KA12 | 60 | 60 | 60 | 60 | 60 | 60 | 60 | 60 |
| $AlCl_3$ | 60 | 60 | 60 | 60 | 60 | 60 | 60 | 60 |
| $AlBr_3$ | — | — | — | — | — | — | — | — |
| Co-catalyst | 15 | 30 | 8 | 4 | 2 | 15 | 15 | 15 |
| Contents of main silanes in reaction solution (%) | | | | | | | | |
| KA12 | 5.6 | 6.8 | 6.9 | 4.5 | 4.6 | 6.8 | 6.4 | 10.8 | 10.6 |
| KA31 | 14.1 | 12.0 | 11.6 | 6.9 | 7.6 | 21.9 | 21.6 | 16.9 | 28.1 |
| KA13 | 18.3 | 10.5 | 10.9 | 6.1 | 5.8 | 21.8 | 23.0 | 20.6 | 30.4 |
| KA22 | 49.2 | 70.6 | 65.0 | 73.2 | 73.5 | 42.4 | 49.0 | 51.7 | 31.0 |
| KA22 yield (%) | 60.0 | 74.5 | 77.5 | 84.5 | 84.2 | 49.0 | 48.0 | 59.3 | 37.1 |

TABLE 2

| | Example | | | | | | | | |
|---|---|---|---|---|---|---|---|---|---|
| | 9 | 10 | 11 | 12 | 13 | 14 | 15 | 16 | 17 |
| Co-catalyst | iron oxide | Ni oxide powder | copper oxide | alumina powder | $TiO_2$ | SnO powder | Mg granules | Mg granules | Mg granules |
| Reaction time (hr) | 5 | 5 | 5 | 5 | 5 | 5 | 5 | 5 | 5 |
| Charge (g) | | | | | | | | | |
| KA31 | 150 | 150 | 150 | 150 | 150 | 150 | 150 | 150 | 150 |
| KA13 | 150 | 150 | 150 | 150 | 150 | 150 | 150 | 150 | 150 |
| KA12 | 60 | 60 | 60 | 60 | 60 | 60 | 60 | 60 | 60 |
| $AlCl_3$ | 60 | 60 | 60 | 60 | 60 | 60 | 60 | 60 | — |
| $AlBr_3$ | — | — | — | — | — | — | — | — | 60 |
| Co-catalyst | 15 | 15 | 15 | 15 | 15 | 15 | 15 | 30 | 15 |

TABLE 2-continued

| | Example | | | | | | | | |
|---|---|---|---|---|---|---|---|---|---|
| | 9 | 10 | 11 | 12 | 13 | 14 | 15 | 16 | 17 |
| Contents of main silanes in reaction solution (%) | | | | | | | | | |
| KA12 | 10.4 | 15.8 | 14.1 | 18.8 | 18.2 | 16.4 | 6.1 | 7.7 | 6.5 |
| KA31 | 32.0 | 36.5 | 37.6 | 37.6 | 38.3 | 36.5 | 21.1 | 18.9 | 15.6 |
| KA13 | 35.1 | 38.2 | 37.7 | 38.5 | 38.9 | 37.8 | 22.4 | 19.0 | 15.7 |
| KA22 | 22.4 | 9.5 | 5.6 | 5.1 | 4.5 | 9.1 | 50.4 | 50.5 | 41.8 |
| KA22 yield (%) | 27.0 | 12.6 | 7.9 | 7.1 | 6.3 | 12.3 | 50.1 | 60.6 | 60.7 |

TABLE 3

| | Example | | | | | |
|---|---|---|---|---|---|---|
| | 18 | 19 | 20 | 21 | 22 | 23 |
| Co-catalyst | Ca hydroxide | ZnO powder | Zn powder | brass | MgSO$_4$ | MgCO$_3$ |
| Reaction time (hr) | 5 | 5 | 5 | 5 | 5 | 5 |
| Charge (g) | | | | | | |
| KA31 | 150 | 150 | 150 | 150 | 150 | 150 |
| KA13 | 150 | 150 | 150 | 150 | 150 | 150 |
| KA12 | 60 | 60 | 60 | 60 | 60 | 60 |
| AlCl$_3$ | 60 | 60 | 60 | 60 | 60 | 60 |
| AlBr$_3$ | — | — | — | — | — | — |
| Co-catalyst | 15 | 15 | 15 | 15 | 15 | 15 |
| Contents of main silanes in reaction solution (%) | | | | | | |
| KA12 | 11.1 | 9.2 | 11.2 | 8.5 | 7.2 | 5.3 |
| KA31 | 18.5 | 21.3 | 34.3 | 29.5 | 23.4 | 18.9 |
| KA13 | 22.7 | 21.7 | 36.2 | 32.0 | 26.3 | 26.1 |
| KA22 | 36.0 | 47.8 | 14.9 | 28.4 | 36.7 | 33.9 |
| KA22 yield (%) | 47.9 | 56.1 | 19.2 | 33.9 | 42.2 | 43.0 |

TABLE 4

| | Comparative Example | | |
|---|---|---|---|
| | 1 | 2 | 3 |
| Co-catalyst | none | none | Mg granules |
| Reaction time (hr) | 5 | 1 | 5 | 13 | 5 |
| Charge (g) | | | | | |
| KA31 | 150 | | 150 | | 150 |
| KA13 | 150 | | 150 | | 150 |
| KA12 | — | | 60 | | 60 |
| AlCl$_3$ | 60 | | 60 | | — |
| AlBr$_3$ | — | | — | | — |
| Co-catalyst | — | | — | | 15 |
| Contents of main silanes in reaction solution (%) | | | | | |
| KA12 | — | 16.7 | 15.1 | 11.2 | 17.9 |
| KA31 | 47.8 | 41.7 | 38.6 | 32.9 | 41.6 |
| KA13 | 47.1 | 41.7 | 40.1 | 33.6 | 40.5 |
| KA22 | 0 | 0 | 2.0 | 21.1 | 0 |
| KA22 yield (%) | 0 | 0 | 2.8 | 26.7 | 0 |

Example 24 and Comparative Example 4

A reactor equipped with a stirrer and a reflux condenser having a dry ice trap was charged with 88 g of tetramethylsilane (KA40) and 150 g of methyltrichlorosilane (KA13) as the organochlorosilane, 46 g of methyldichloro silane (KA12) as the SiH group-containing compound, 46 g of AlCl$_3$ as the primary catalyst, and an amount shown in Table 5 of MgO as the co-catalyst. Reaction was effected with stirring. Heating was completed within one hour and the reaction time was 5 hours during which the temperature was kept constant at 42° C. After the completion of reaction, the reaction system was cooled to room temperature within one hour.

Compositional analysis of the charge and the reaction solution was carried out by gas chromatography. From these results, the yield of dimethyldichlorosilane (KA22) was computed. The composition of the reaction solution is shown in Table 5 together with the yield.

TABLE 5

| | Example 24 | Comparative Example 4 |
|---|---|---|
| Co-catalyst | MgO | none |
| Reaction time (hr) | 5 | 5 |
| Charge (g) | | |
| KA40 | 88 | 88 |
| KA13 | 150 | 150 |
| KA12 | 46 | 46 |
| AlCl$_3$ | 46 | 46 |
| Co-catalyst | 15 | — |
| Contents of main silanes in reaction solution (%) | | |
| KA40 | 0 | 0 |
| KA12 | 1.7 | 15.0 |
| KA31 | 17.6 | 5.6 |
| KA13 | 6.7 | 53.8 |
| KA22 | 62.1 | 1.4 |
| KA22 yield (%) | 88.0 | 8.2 |

It is evident from the foregoing Examples that the use of co-catalysts according to the invention allows the reaction to proceed at a very high rate even at low temperature. As seen from changes with time of the reaction products of Example 1 and Comparative Example 2, the co-catalysts according to the invention have a significant effect of reducing the reaction time (or accelerating the reaction rate).

The present invention enables disproportionation reaction of organochlorosilanes under atmospheric pressure and at a low temperature at which no substantial sublimation of AlCl$_3$ or the like occurs. This allows the reaction equipment to be simple and improves the safety of reaction. Useful diorganodichlorosilanes are produced at a significantly higher rate than less-useful silanes and waste silanes which are discarded.

Japanese Patent Application No. 2001-247800 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A process for preparing a diorganodichlorosilane, comprising the step of subjecting an organochlorosilane to disproportionation reaction in the co-presence of a compound having a hydrogen atom directly bonded to a silicon atom and in the presence of a primary catalyst of $AlCl_3$ or $AlBr_3$ and a co-catalyst selected from the group consisting of Mg, Al, Ca, Ti, Fe, Ni, Cu, Zn and Sn, compounds of these metals excluding $AlCl_3$ and $AlBr_3$, and mixtures thereof.

2. The process of claim 1 wherein the co-catalyst is used in an amount of 0.1 to 20 parts by weight per 100 parts by weight of the organochlorosilane and 1 to 50 parts by weight per 100 parts by weight of the primary catalyst.

3. The process of claim 2, wherein the co-catalyst is used in an amount of 1 to 10 parts by weight per 100 parts by weight of organochlorosilane and 2 to 30 parts by weight per 100 parts by weight of the primary catalyst.

4. The process of claim 1 wherein the metal compound is an alloy, oxide, chloride, carbonate, sulfate or hydroxide.

5. The process of claim 1 wherein the compound having a hydrogen atom directly bonded to a silicon atom has the following general formula:

$$R_aH_bSiCl_{4-a-b}$$

wherein R is a monovalent hydrocarbon group, "a" is an integer of 0 to 3, "b" is an integer of 1 to 4, and a+b is an integer of 1 to 4.

6. The process of claim 5, wherein the compound having a hydrogen atom directly bonded to the silicon atom is methyldichlorosilane or dimethylchlorosilane.

7. The process of claim 1 wherein the disproportionation reaction is effected at a temperature of not higher than 100° C.

8. The process of claim 5, wherein the disproportionation reaction is effected at room temperature to 80° C.

9. The process of claim 1, wherein the organochlorosilane comprises an organic group which is a monovalent hydrocarbon having 1 to 6 carbon atoms.

10. The process of claim 1, wherein the monovalent hydrocarbon is methyl, ethyl or phenyl.

11. The process of claim 1, wherein the co-catalyst is at least one selected from the group consisting of magnesium oxide, aluminum oxide, calcium oxide, titanium oxide, iron oxide, nickel oxide, copper oxide, zinc oxide, tin oxide, calcium hydroxide, magnesium chloride, zinc chloride, magnesium carbonate, magnesium sulfate, and brass.

* * * * *